US009212122B2

(12) United States Patent
Blum et al.

(10) Patent No.: US 9,212,122 B2
(45) Date of Patent: Dec. 15, 2015

(54) PROCESS FOR INHIBITING UNWANTED FREE-RADICAL POLYMERIZATION OF ACRYLIC ACID PRESENT IN A LIQUID PHASE P

(75) Inventors: Till Blum, Kuantan (MY); Peter Zurowski, Landau (DE); Tobias Johannes Korn, Ludwigshafen (DE); Sylke Haremza, Neckargemünd (DE); Thorsten Friese, Mannheim (DE); Friedrich-Georg Martin, Heidelburg (DE); Ulrich Jäger, Römerberg (DE); Steffen Rissel, Kirchheim (DE); Volker Schliephake, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 45 days.

(21) Appl. No.: 13/253,245

(22) Filed: Oct. 5, 2011

(65) Prior Publication Data
US 2012/0085969 A1 Apr. 12, 2012

Related U.S. Application Data

(60) Provisional application No. 61/391,102, filed on Oct. 8, 2010.

(30) Foreign Application Priority Data

Oct. 8, 2010 (DE) .......................... 10 2010 042 216

(51) Int. Cl.
C07C 51/50 (2006.01)
(52) U.S. Cl.
CPC ...................................... C07C 51/50 (2013.01)
(58) Field of Classification Search
CPC ....................................................... C07C 51/50
USPC .......................... 252/182.28, 182.29, 400.53
See application file for complete search history.

(56) References Cited

U.S. PATENT DOCUMENTS

| | | | |
|---|---|---|---|
| 4,317,926 A | 3/1982 | Sato et al. | |
| 5,198,578 A | 3/1993 | Etzkorn et al. | |
| 6,441,228 B2 | 8/2002 | Nakahara et al. | |
| 6,888,025 B2 | 5/2005 | Hirao et al. | |
| 6,966,973 B2 | 11/2005 | Nakahara et al. | |
| 7,109,372 B2 | 9/2006 | Hirao et al. | |
| 7,319,167 B2 | 1/2008 | Nakahara et al. | |
| 7,332,624 B2 | 2/2008 | Nishimura et al. | |
| 2004/0242826 A1 | 12/2004 | Nishimura | |
| 2007/0021633 A1* | 1/2007 | Yada et al. | 562/600 |
| 2007/0149807 A1 | 6/2007 | Dieterle et al. | |
| 2010/0022734 A1 | 1/2010 | Blum et al. | |
| 2010/0130778 A1 | 5/2010 | Sakamoto et al. | |

FOREIGN PATENT DOCUMENTS

| | | |
|---|---|---|
| DE | 24 49 780 A1 | 4/1976 |
| DE | 35 21 458 A1 | 12/1985 |
| DE | 43 08 087 A1 | 9/1994 |
| DE | 43 35 172 A1 | 4/1995 |
| DE | 44 36 243 A1 | 4/1996 |
| DE | 195 01 325 A1 | 7/1996 |
| DE | 196 06 877 A1 | 8/1997 |
| DE | 196 27 847 A1 | 1/1998 |
| DE | 196 27 850 A1 | 1/1998 |
| DE | 197 34 171 A1 | 2/1999 |
| DE | 198 35 247 A1 | 2/1999 |
| DE | 197 40 252 A1 | 3/1999 |
| DE | 197 40 253 A1 | 3/1999 |
| DE | 198 10 962 A1 | 9/1999 |
| DE | 198 37 520 A1 | 2/2000 |
| DE | 697 01 590 T2 | 9/2000 |
| DE | 199 24 532 A1 | 11/2000 |
| DE | 199 24 533 A1 | 11/2000 |
| DE | 696 12 797 T2 | 9/2001 |
| DE | 100 28 582 A1 | 12/2001 |
| DE | 101 15 277 A1 | 6/2002 |
| DE | 101 31 297 A1 | 1/2003 |
| DE | 102 35 847 A1 | 8/2003 |
| DE | 102 23 058 A1 | 12/2003 |
| DE | 103 36 386 A1 | 3/2004 |
| DE | 102 43 625 A1 | 4/2004 |
| DE | 102 45 585 A1 | 4/2004 |
| DE | 102 46 119 A1 | 4/2004 |
| DE | 102 47 240 A1 | 4/2004 |
| DE | 103 32 758 A1 | 5/2004 |
| DE | 10 2005 052 917 A1 | 10/2007 |
| DE | 10 2007 029 053 A1 | 1/2008 |
| DE | 10 2007 004 960 A1 | 7/2008 |
| DE | 10 2008 040 799 A1 | 12/2008 |
| DE | 10 2007 055 086 A1 | 5/2009 |
| DE | 10 2009 027 401 A1 | 2/2010 |
| DE | 10 2008 041 573 A1 | 3/2010 |
| EP | 0 117 146 A1 | 8/1984 |
| EP | 0 253 409 A2 | 1/1988 |
| EP | 0 608 838 A2 | 8/1994 |
| EP | 0 695 736 A1 | 2/1996 |
| EP | 0 722 926 A1 | 7/1996 |
| EP | 0 765 856 A1 | 4/1997 |
| EP | 0 770 592 A1 | 5/1997 |

(Continued)

OTHER PUBLICATIONS

Material Data Safety Sheet for Propylene, issued by Sanyo Petrochemical Co., Ltd., (Feb. 23, 2010).

(Continued)

*Primary Examiner* — Peter F Godenschwager
(74) *Attorney, Agent, or Firm* — Oblon, McClelland, Maier & Neustadt, L.L.P.

(57) ABSTRACT

A process for inhibiting unwanted free-radical polymerization of acrylic acid present in a liquid phase P whose acrylic acid content is at least 10% by weight and which, based on the weight of the acrylic acid present therein, additionally comprises at least 100 ppm by weight of propionic acid and at least 100 ppm by weight of glyoxal, in which at least one chemical compound of the element copper is added to the liquid phase P, and the resulting liquid phases P to which a chemical compound of the element copper has been added.

36 Claims, No Drawings

(56) References Cited

FOREIGN PATENT DOCUMENTS

| | | |
|---|---|---|
| EP | 0 778 255 A1 | 6/1997 |
| EP | 0 792 867 A2 | 9/1997 |
| EP | 0 854 129 A1 | 7/1998 |
| EP | 0 920 408 B1 | 6/1999 |
| EP | 0 982 287 A1 | 3/2000 |
| EP | 0 982 288 A2 | 3/2000 |
| EP | 0 982 289 A2 | 3/2000 |
| EP | 1 015 410 B1 | 7/2000 |
| EP | 1 015 411 B1 | 7/2000 |
| EP | 1 041 062 A2 | 10/2000 |
| EP | 1 066 239 B1 | 1/2001 |
| EP | 1 066 240 B1 | 1/2001 |
| EP | 1 068 174 B1 | 1/2001 |
| EP | 1 116 709 | 7/2001 |
| EP | 1 298 120 A2 | 4/2003 |
| EP | 1 388 532 A1 | 2/2004 |
| EP | 1 388 533 A1 | 2/2004 |
| EP | 1 396 484 A1 | 3/2004 |
| EP | 1 484 303 A2 | 12/2004 |
| EP | 1 484 308 A1 | 12/2004 |
| EP | 1 484 309 A1 | 12/2004 |
| EP | 1 710 227 A1 | 10/2006 |
| JP | 1-135519 | 5/1989 |
| JP | 2001-199931 A | 7/2001 |
| JP | 2001-348359 | 12/2001 |
| JP | 2002-258046 A | 9/2002 |
| JP | 2004/091432 | 3/2004 |
| JP | 2004-359615 A | 12/2004 |
| JP | 2009/520747 | 5/2009 |
| WO | WO 98/01414 A1 | 1/1998 |
| WO | WO 98/01415 A1 | 1/1998 |
| WO | WO 99/50219 A1 | 10/1999 |
| WO | WO 00/53560 A1 | 9/2000 |
| WO | WO 00/53561 A1 | 9/2000 |
| WO | WO 01/92190 A1 | 12/2001 |
| WO | WO 01/96270 A2 | 12/2001 |
| WO | WO 01/96271 A2 | 12/2001 |
| WO | WO 02/09839 A1 | 2/2002 |
| WO | WO 02/055469 A1 | 7/2002 |
| WO | WO 03/011804 A2 | 2/2003 |
| WO | WO 03/041832 A1 | 5/2003 |
| WO | WO 03/078378 A1 | 9/2003 |
| WO | WO 2004/018089 A1 | 3/2004 |
| WO | WO 2004/035514 A1 | 4/2004 |
| WO | WO 2004/063138 A1 | 7/2004 |
| WO | WO 2005/035478 A2 | 4/2005 |
| WO | WO 2005/042459 A1 | 5/2005 |
| WO | WO 2005/047224 A1 | 5/2005 |
| WO | WO 2005/047226 A1 | 5/2005 |
| WO | WO 2005/073160 A1 | 8/2005 |
| WO | WO 2006/002713 A1 | 1/2006 |
| WO | WO 2006/092272 A2 | 9/2006 |
| WO | WO 2006/114506 A1 | 11/2006 |
| WO | WO 2006/136336 A2 | 12/2006 |
| WO | WO 2007/006370 A1 | 1/2007 |
| WO | WO 2007/074044 A1 | 7/2007 |
| WO | WO 2007/074045 A1 | 7/2007 |
| WO | WO 2007/090991 A2 | 8/2007 |
| WO | WO 2008/090190 A1 | 7/2008 |
| WO | WO 2008/146613 A1 | 12/2008 |
| WO | WO 2010/012586 A1 | 2/2010 |
| WO | WO 2010/074177 A1 | 7/2010 |
| WO | WO 2011/000808 A2 | 1/2011 |

OTHER PUBLICATIONS

Third Party Observations, issued May 27, 2014, in European Patent Application No. 11771064.0.

* cited by examiner

PROCESS FOR INHIBITING UNWANTED FREE-RADICAL POLYMERIZATION OF ACRYLIC ACID PRESENT IN A LIQUID PHASE P

CROSS REFERENCE TO RELATED APPLICATION

This application claims the benefit of U.S. Provisional Application No. 61/391,102, filed on Oct. 8, 2010, and claims priority to German Application No. 10 2010 042 216.9, filed on Oct. 8, 2010.

The present invention relates to a process for inhibiting unwanted free-radical polymerization of acrylic acid present in a liquid phase P whose acrylic acid content is at least 10% by weight and which, based on the weight of the acrylic acid present therein, additionally comprises at least 100 ppm by weight of propionic acid and at least 100 ppm by weight of glyoxal, and to the liquid phases obtained in the execution of the process.

Acrylic acid is an important monomer which finds use as such, in the form of its salts and/or in the form of its esters (e.g. alkyl esters) for production of polymers which are used, for example, as adhesives or as water-superabsorbing materials (cf., for example, WO 02/055469 and WO 03/078378).

Acrylic acid can be prepared, for example, by heterogeneously catalyzed partial oxidation of a $C_3$ precursor compound (e.g. propylene, propane, acrolein, propionaldehyde, propionic acid, propanol and/or glycerol) in the gas phase (cf., for example, WO 2010/012586, U.S. Pat. No. 5,198,578, EP-A 1 710 227, EP-A 1 015 410, EP-A 1 484303, EP-A 1 484 308, EP-A 1 484 309, US-A 2004/0242826, WO 2006/136336, DE-A 10 028 582 and WO 2007/074044).

In principle, in the context of such a heterogeneously catalyzed partial gas phase oxidation, what is obtained is not pure acrylic acid but merely a product gas mixture which comprises acrylic acid and, in addition to acrylic acid, also comprises constituents other than acrylic acid, from which the acrylic acid has to be removed.

Both the type and the proportion of the constituents other than acrylic acid in the product gas mixture can be influenced by factors including the selection of the $C_3$ precursor compound, the catalyst used, the reaction conditions under which the heterogeneously catalyzed partial gas phase oxidation is performed, the type and amount of the contaminating constituents other than the $C_3$ precursor compound which are present in the $C_3$ precursor compound used as the raw material, and the selection of the diluent gases which generally dilute the reactants in the reaction gas mixture (cf., for example, DE-A 10 131 297, DE-A 10 2005 0529 17, WO 2007/074044 and DE-A 10 028 582).

To remove the acrylic acid from the product gas mixture of the heterogeneously catalyzed partial gas phase oxidation of a $C_3$ precursor compound, a combination of different separating processes is normally employed in order to achieve a purity appropriate for the subsequent end use of the acrylic acid in a very economically viable manner. The specific combination employed depends upon factors including the type and amount of the constituents other than acrylic acid which are present in the product gas mixture.

A feature common essentially to all possible combinations of separating processes for removal of acrylic acid from the product gas mixture of a heterogeneously catalyzed partial gas phase oxidation of a $C_3$ precursor compound is that, optionally after direct and/or indirect cooling of the aforementioned product gas mixture, acrylic acid present in the product gas mixture is converted to the condensed (especially liquid) phase in a basic removal step.

This can be undertaken, for example, by absorption into a suitable solvent (for example water, high-boiling organic solvents, aqueous solutions) and/or by partial or essentially full condensation (e.g. fractional condensation) (cf., for example, the documents EP-A 1 388 533, EP-A 1 388 532, DE-A 10 235 847, EP-A 792 867, WO 98/01415, U.S. Pat. No. 7,332, 624 B2, U.S. Pat. No. 6,888,025 B2, U.S. Pat. No. 7,109,372 B2, EP-A 1 015 411, EP-A 1 015 410, WO 99/50219, WO 00/53560, WO 02/09839, DE-A 10 235 847, WO 03/041832, DE-A 10 223 058, DE-A 10 243 625, DE-A 10 336 386, EP-A 854129, U.S. Pat. No. 7,319,167 B2, U.S. Pat. No. 4,317,926, DE-A 1 983 752 0, DE-A 1 960 687 7, DE-A 1 950 132 5, DE-A 10 247 240, DE-A 1 974 025 3, EP-A 695 736, EP-A 982 287, EP-A 1 041 062, EP-A 117 146, DE-A 4 308 087, DE-A 4 335 172, DE-A 4 436 243, DE-A 19 924 532, DE-A 10 332 758 and DE-A 19 924 533). An acrylic acid removal can also be undertaken as in EP-A 982 287, EP-A 982 289, DE-A 10 336 386, DE-A 10 115 277, DE-A 19 606 877, DE-A 19 740 252, DE-A 19 627 847, EP-A 920 408, EP-A 10 681 74, EP-A 10 662 39, EP-A 10 662 40, WO 00/53560, WO 00/53561, DE-A 10 053 086 and EP-A 982 288. Suitable removal methods are also the processes described in documents WO 2004/063138, WO 2008/090190, WO 2004/ 035514, DE-A 10 243 625 and DE-A 10 235 847.

With the acrylic acid, constituents other than acrylic acid which are present in the product gas mixture of the heterogeneously catalyzed partial gas phase oxidation are normally also converted to the condensed phase.

Documents WO 2007/074044, WO 2007/074045 and DE-A 10 2007 029 053 disclose that, when the reaction gas mixture comprises cyclopropane as an impurity, in the context of the heterogeneously catalyzed partial gas phase oxidation of the $C_3$ precursor compound (e.g. propylene) to acrylic acid, elevated amounts of propionic acid generally occur as a by-product in the product gas mixture, and this propionic acid is generally converted to the condensed phase with the acrylic acid in significant proportions in the above-described basic removal of the acrylic acid from the product gas mixture. Elevated amounts of propionic acid are normally also formed in the context of a heterogeneously catalyzed partial gas phase oxidation of, for example, propylene and/or acrolein to acrylic acid when the $O_2$ and propylene and/or acrolein reactants in the reaction gas mixture are diluted by elevated amounts of n-propane (cf., for example, DE-A 10028582).

Presence of propionaldehyde in the reaction gas mixture of the partial oxidation of the $C_3$ precursor compound generally likewise causes increased propionic acid by-product formation (cf., for example, WO 2010/074177).

Documents DE-A 10 2009 0274 01, DE-A 10 2008 041 573, DE-A 10 2008 040 799, EP-A 1 298 120 and EP-A 1 396 484 disclose that, when the reaction gas mixture of the heterogeneously catalyzed partial gas phase oxidation of the $C_3$ precursor compound to acrylic acid comprises $C_2$ impurities, for example ethylene, in the context of the heterogeneously catalyzed partial gas phase oxidation, elevated amounts of the aldehyde (monomeric) glyoxal generally occur as a by-product in the product gas mixture, and that (monomeric) glyoxal is typically converted to the condensed phase with the acrylic acid in significant proportions in the above-described basic removal of the acrylic acid from the product gas mixture.

When the reaction gas mixtures of the heterogeneously catalyzed partial gas phase oxidation of the $C_3$ precursor compound (for example of propylene) comprise both the aforementioned $C_3$ and $C_2$ impurities, the described basic removal of the acrylic acid from the product gas mixture of the heterogeneously catalyzed partial gas phase oxidation normally gives condensed phase which comprises, as well as acrylic acid, additionally propionic acid and glyoxal.

EP-A 770592 discloses that very small amounts of aldehydic impurities, for example glyoxal, present in acrylic acid can significantly impair the properties of the acrylic acid. For instance, according to the teaching of EP-A 770 592, the individual aldehyde components within an acrylic acid should be below 1 ppm in order to achieve the optimal product qualities in the context of the use of such acrylic acid in especially free-radical polymerization reactions, for example for production of superabsorbent polymers or of polymers effective as dispersants for oil drilling mud or as flocculants.

It is common knowledge (e.g. DE-A 10 028 582) that both propionic acid and the esters thereof with lower alkanols are exceptionally intense and unpleasant-smelling odor carriers, and the propionic acid should therefore be removed from the acrylic acid prior to, for example, an esterification of acrylic acid with lower alkanols.

The separating steps to be employed in order to remove the acrylic acid in the desired purity from a liquid phase which is obtained in the context of the basic removal described and comprises the acrylic acid target product and the unwanted glyoxal and propionic acid by-products may, according to the objective and type and amount of other unwanted secondary components additionally present, be a wide variety of different combinations of, for example, adsorptive, extractive, desorptive, distillative, stripping, rectificative, azeotropic distillation, azeotropic rectification and crystallizative processes.

In the context of the aforementioned separating processes, a wide variety of different liquid phases comprising the acrylic acid target product and the unwanted glyoxal and propionic acid by-products occur in different proportions, which, for example, have to be stored intermediately and/or thermally stressed by supply of heat.

This is disadvantageous in that both long residence times and thermal stress increase the probability of unwanted free-radical polymerization of the acrylic acid present in the liquid phase.

The latter is all the more true in that the physical similarity of acrylic acid and propionic acid necessitates increased residence times in the application of noncrystallizative thermal separating processes in the separating apparatus in order to achieve significant separating action, and monomeric glyoxal promotes the tendency of acrylic acid to unwanted free-radical polymerization to a considerably greater degree than other possible impurities (cf. DE-A 102008041573, DE-A 102008040799 and DE-A 102009027401).

It is common knowledge that addition of inhibitors (also known as retarders) to acrylic acid present in the liquid phase can counteract the polymerization-promoting influence of residence time and thermal stress (cf., for example, "Polymerisationsinhibierung von (Meth-)Acrylaten [Inhibition of polymerization of (meth)acrylates], thesis by Dipl.-lng. Holger Becker, Technische Universität Darmstadt, 2003").

The variety of the inhibitors recommended for these purposes in the prior art is virtually unlimited (cf., for example, EP-A 765 856 and DE 69 701 590 T2, which acknowledge a small section of these inhibitors), and also comprises compounds of the element copper (cf., for example, JP-A 2001348359).

According to EP-A 1396484 (especially lines 16 and 17 of column 2), however, none of the known inhibitor systems is satisfactory. Furthermore, the diversity of the inhibitors recommended in the prior art, according to EP-A 1 396 484 (e.g. column 7 paragraph [0024] and column 1 lines 40 to 44), does not comprise any significant preference.

More particularly, EP-A 1 396 484 states, in column 3 lines 5 to 10, that the known inhibitors are capable of comparatively effectively inhibiting the unwanted free-radical polymerization of acrylic acid due to thermal stress thereon, but that, in particular, the inhibiting action thereof with respect to inducement and/or promotion of unwanted free-radical polymerization of acrylic acid by impurities present therein, such as glyoxal, is insufficient.

One means of overcoming the difficulties described is to prevent the formation of unwanted by-products such as propionic acid and glyoxal in the heterogeneously catalyzed partial gas phase oxidation of $C_3$ precursor compounds (these are precursor compounds which have three carbon atoms) of acrylic acid to acrylic acid (for example by skilful catalyst selection (cf., for example, JP-A 11-35519) or by use of high-purity $C_3$ precursor raw materials (thus obtaining, for example, reaction gas mixtures comprising neither $C_2$ impurities or n-propane nor cyclopropane; DE-A 3521458 describes, for example, the possibility of purification of propylene prepared from n-propane, and documents WO 2004/018089 and WO 01/92190 describe, for example, the preparation of propylene from methanol (an altered raw material basis)). However, this is disadvantageous in that the expenditures required for this purpose impair the economic viability of the acrylic acid preparation.

Against this background, it was an object of the present invention to provide a process for inhibiting unwanted free-radical polymerization of acrylic acid present in a liquid phase P whose acrylic acid content is at least 10% by weight and which, based on the weight of the acrylic acid present therein, additionally comprises at least 100 ppm by weight of propionic acid and at least 100 ppm by weight of glyoxal, which, more particularly, effectively counteracts the inducement and/or promotion of unwanted free-radical polymerization of acrylic acid by the glyoxal present therein.

The above object is achieved by a process for inhibiting unwanted free-radical polymerization of acrylic acid present in a liquid phase P whose acrylic acid content is at least 10% by weight and which, based on the weight of the acrylic acid present therein, additionally comprises at least 100 ppm by weight of propionic acid and at least 100 ppm by weight of glyoxal, wherein at least one chemical compound of the element copper is added to the liquid phase P.

The process according to the invention is based on, compared to the existing prior art knowledge, the exciting experimental finding that glyoxal in the presence of compounds of the element copper does not promote unwanted free-radical polymerization of acrylic acid but inhibits (retards) it.

As a result, for example, of reaction with secondary constituents having hydroxyl groups (e.g. $H_2O$, alcohols such as ethanol, etc.), monomeric glyoxal

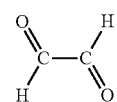

is capable of forming hemiacetals and/or acetals. Such hemiacetals and/or acetals generally have the polymerization-promoting action typical of monomeric glyoxal only to a significantly lesser degree, if at all.

However, in the case of hemiacetals or acetals of glyoxal, the formation reaction is frequently a markedly reversible reaction, and therefore monomeric glyoxal is formed again from these hemiacetals or acetals, for example under the action of elevated temperature or in the event of removal of glyoxal from the corresponding equilibrium, and then has a corresponding influence on the unwanted free-radical polymerization.

In the case of water as a secondary constituent having hydroxyl groups, for example, the following markedly reversible acetal formation reactions are known (in this case, reference is also made to hydrates of glyoxal):

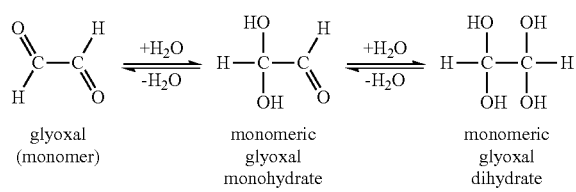

glyoxal (monomer)     monomeric glyoxal monohydrate     monomeric glyoxal dihydrate Both glyoxal hydrates mentioned above form even under comparatively mild conditions (relatively low temperatures, limited water contents are sufficient).

The terminology "monomeric" glyoxal monohydrate and "monomeric" glyoxal dihydrate is used for the purpose of delimiting the terms from "polyglyoxal" hydrates and "oligoglyoxal" hydrates.

The following diglyoxal hydrates and triglyoxal hydrates are shown by way of example:

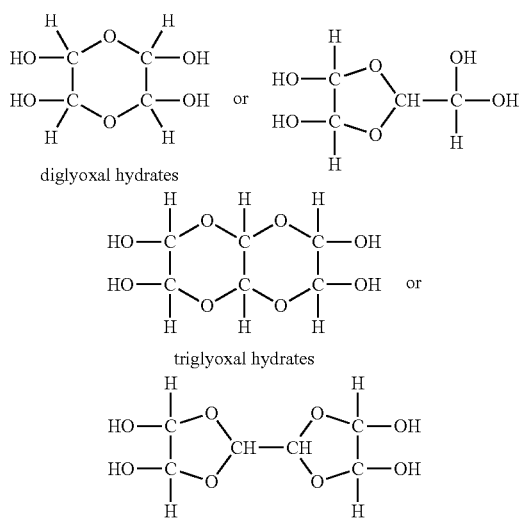

diglyoxal hydrates triglyoxal hydrates

The formation of the polyglyoxal hydrates probably proceeds via the monomeric glyoxal dihydrate as an intermediate (cf. also DE-A 102008041573, DE-A 102008040799 and DE-A 102009027401).

In contrast to the formation of the monomeric glyoxal hydrates, the formation of the polyglyoxal hydrates requires elevated temperatures (generally, they are not formed to a significant degree until temperatures above 50° C.) and/or prolonged reaction times.

For the reasons mentioned above, in this document, the term "glyoxal" (unless explicitly stated otherwise, or unless at least one additional characterization, for example "monomeric" glyoxal or "di" glyoxal "hydrate", or "monomeric" glyoxal "monohydrate" is added to the term "glyoxal") shall therefore include not only monomeric glyoxal but also glyoxal chemically bound reversibly in the form of, for example, acetals and/or hemiacetals of monomeric glyoxal.

The solitary term "glyoxal" in this document thus always means the total amount of monomeric glyoxal and reversibly bound glyoxal.

In this document, glyoxal contents reported in "% by weight" accordingly always mean the total amount of monomeric glyoxal and reversibly bound glyoxal present, for example in monomeric glyoxal monohydrate and in monomeric glyoxal dihydrate, but always calculated as "monomeric glyoxal" (in other words, they mean the proportion by weight of the total amount of $H_2C_2O_2$ units present).

This is especially relevant for the inventive procedure in that water is normally the main by-product of a heterogeneously catalyzed partial gas phase oxidation of a $C_3$ precursor compound of acrylic acid to acrylic acid. Furthermore, steam, for example due to its comparatively elevated molar heat capacity, is frequently also used as a diluent gas in the reaction mixture for heterogeneously catalyzed partial gas phase oxidations of $C_3$ precursor compounds to acrylic acid (cf., for example, EP-A 253 409). The basic removal of acrylic acid from the product gas mixture of a heterogeneously catalyzed partial gas phase oxidation of a $C_3$ precursor compound to acrylic acid therefore frequently passes through liquid phases which comprise, as well as acrylic acid, propionic acid and glyoxal, also water. In principle, however, glyoxal hydrates may also be formed even in the product gas mixture of the heterogeneously catalyzed partial gas phase oxidation of the $C_3$ precursor compound of acrylic acid.

Incidentally, water or aqueous solutions are frequently also recommended in the prior art as absorbents for an absorptive basic removal from the product gas mixture of the gas phase partial oxidation of the $C_3$ precursor compound (cf., for example, EP-A 1 298 120 and U.S. Pat. No. 7,332,624 B2).

The glyoxal content in a liquid phase P to be treated in accordance with the invention (or in another liquid phase) (i.e. the total content in the liquid phase P of monomeric glyoxal and glyoxal bound reversibly in compounds such as monomeric glyoxal monohydrate and monomeric glyoxal dihydrate (for example, monomeric glyoxal is also capable of reversibly forming hemiacetals and/or acetals with alcohols such as ethanol)) is determined in the context of the present patent application as follows:

First, a derivatization solution D is prepared. To this end, 2.0 g of a 50% by weight solution of 2,4-dinitrophenylhydrazine (manufacturer: Aldrich, purity: ≥97%) is dissolved at a temperature of 25° C. in 62 ml of 37.0% by weight aqueous hydrochloric acid (manufacturer: Aldrich, purity: ≥99.999%). The resulting solution is subsequently (likewise at a temperature of 25° C.) stirred into 335 g of distilled water. After stirring at 25° C. for 1 hour, the derivatization solution D is obtained by filtration as the resulting filtrate.

To determine the glyoxal content in a liquid phase P, 1 g (this amount can be increased correspondingly if required) of the derivatization solution D is weighed into a screwtop bottle whose capacity is 10 ml. Subsequently, a sample of the liquid phase P is weighed into the screwtop bottle thus filled, the amount of which is in the range from 0.15 to 2.0 g.

The entire contents of the screwtop bottle are then mixed by shaking and then left to stand at a temperature of 25° C. over a period of 10 minutes. During this time, the corresponding hydrazone H of monomeric glyoxal forms from the monomeric glyoxal present in the screwtop bottle by chemical reaction with 2,4-dinitrophenylhydrazine. During this time, the 2,4-dinitrophenylhydrazine, however, also removes the monomeric glyoxal present in bound form in the monomeric glyoxal monohydrate and glyoxal dihydrate present in the screwtop bottle therefrom in the form of the hydrazone H (a corresponding removal of monomeric glyoxal from polyglyoxal hydrates present in the screwtop bottle, in contrast, essentially does not take place).

Addition of 0.5 g of glacial acetic acid (manufacturer: Aldrich, purity: ≥99.8%) to the screwtop bottle subsequently freezes the hydrazone formation which has occurred. When the addition of acetic acid is accompanied by formation of solid precipitate, further acetic acid is added gradually in order to redissolve the precipitate formed (but the total amount of acetic acid added must not exceed 1.0 g). When the precipitate formed still has not gone into solution even on attainment of the limit (1.0 g) in the total amount of acetic acid addition allowed, 0.5 g of dimethyl phthalate is weighed in. If this too is incapable of dissolving the precipitate formed, the amount of dimethyl phthalate added is increased gradually in order to bring about this dissolution (but the total amount of dimethyl phthalate added must not exceed 1.0 g). When the precipitate formed still has not gone into solution even on attainment of the limit (1.0 g) in the total amount of dimethyl phthalate addition allowed, 2 g of a mixture G of 9 g of acetonitrile and 1 g of dimethyl phthalate are added. If this addition too is incapable of dissolving the precipitate, the amount of mixture G added is increased gradually in order to bring about this dissolution. Normally, the total amount of mixture G added in order to bring about the dissolution of the precipitate does not exceed 5 g (all above dissolution tests are carried out at 25° C.).

The solution of the hydrazone H obtained in the screwtop bottle as described is subsequently analyzed for its hydrazone content by means of HPLC (High Pressure Liquid Chromatography) using the following operating conditions (the molar amount thereof results directly in the molar amount of glyoxal present in the liquid phase P):

Chromatography column to be used: Waters Symmetry C18, 150×4.6 mm, 5 µm (from Waters Associates, Milford, Mass., USA);
Injection volume of the solution to be analyzed: 50 µl (time t=0);
Temperature: 40° C.;
Eluent flow rate: 1.5 ml/min;
Analysis time: 17 min;
Equilibration time: 8 min;
Eluent: in the period t from >0 min to 15 min, a mixture of 30% by weight of acetonitrile, 50% by weight of water and 20% by weight of tetrahydrofuran (each HPLC grade);
in the period from >15 min to 17 min, a mixture of 65% by weight of acetonitrile, 30% by weight of water and 5% by weight of tetrahydrofuran;
in the period from >17 min to 25 min, a mixture of 30% by weight of acetonitrile, 50% by weight of water and 20% by weight of tetrahydrofuran (then the column is equilibrated and ready for use again for the next analysis).

The retention time of the glyoxal as the hydrazone H is 7.613 min under the above conditions.

The analysis is effected by means of monochromatic radiation of wavelength 365 nm.

The analysis method employed is absorption spectroscopy.

The variation of the eluent over the elution time ensures an increased separating action (in general, the liquid phase P, as well as glyoxal, also comprises other by-product aldehydes and/or by-product ketones which form the particular corresponding hydrazone with 2,4-dinitrophenylhydrazine).

To calibrate the HPLC method, appropriately in application terms, a solution of monomeric glyoxal in methanol will be used, which comprises 50 ppm by weight of monomeric glyoxal (cf. DE-A 10 2008 041 573 and DE-A 10 2008 040 799).

For this purpose, it is treated by means of the derivatization solution D as described above and then subjected to the HPLC analysis described.

The chemical compounds of the element copper used for the process according to the invention may be either compounds which have the copper in the +2 oxidation state or compounds in which the copper is present in the +1 oxidation state, preference being given in accordance with the invention to addition of the former copper compounds.

In principle, the compound of the element copper to be added to the liquid phase P may be finely dispersed in the liquid phase P (for example as a fine solid or as dispersed fine liquid droplets (optionally of a solution comprising the copper compound in dissolved form)).

Preferably in accordance with the invention, the copper compound to be added to the liquid phase P is, however, dissolved in the liquid phase P. The liquid phase P may itself be a solution or a liquid phase in a system consisting of a plurality of liquid phases. Preferably, in the process according to the invention, salts of copper in which the particular copper cation may also be present in complexed form are added to the liquid phase P.

Examples of copper compounds suitable for the process according to the invention are copper(II) phenoxide, copper(II) acetylacetonate, copper(II) gluconate, copper(II) tartrate, copper(II) acetate, copper(II) formate, copper(II) nitrate, copper(II) hydroxide, copper(II) sulfate, copper(II) carbonate, copper(II) naphthenate, copper(II) acrylate, copper(II) halides, for example copper(II) chloride, copper(II) salicylate, copper(II) sulfonate, copper(II) propionate, copper(II) octanoate, each of which may also have water of hydration. Additionally suitable are copper(I) compounds such as CuCl, CuCN, CuI, CuBr, Cu(I) acetate, $Cu_2SO_4$, $Cu_2O$ and CuCN, but also salts of complex copper(I) anions such as $Cu(CN)_4^{3-}$, or complex copper(I) cations such as $Cu(NH_3)_4^+$. Copper(I) salts are less suitable as an addition to aqueous liquid phases P, since the $Cu^+$ tends to disproportionate therein.

Additionally suitable for the inventive purposes are the copper(II) salts of carbamic acid and the N-substituted derivatives thereof (the preparation of corresponding carbamate solutions is described, for example, by DE 6961279 T2)

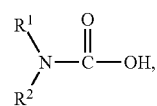

the copper(II) salts of the thiocarbamic acids which are unknown in the free state

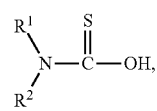

and especially the copper(II) salts of the dithiocarbamic acids

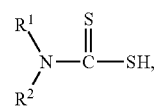

among which the latter are preferred in accordance with the invention (especially for aqueous solutions).

In all aforementioned cases, $R^1$, $R^2$ are each independently hydrogen or an organic radical. The latter are, advantageously in accordance with the invention, a methyl, ethyl, propyl (n-propyl or isopropyl), butyl (n-butyl, or isobutyl, or tert-butyl), pentyl (n-pentyl or cyclopentyl), hexyl (n-hexyl or cyclohexyl), methylcyclohexyl, benzyl, ethylphenyl, phenylethyl, xylyl or a phenyl group. Especially suitable for the inventive procedure are all copper(II) dithiocarbamates listed in JP-A 2001348359.

These are especially copper(II) dimethyldithiocarbamate, copper(II) diethyldithiocarbamate, copper(II) di-n-propyldithiocarbamate, copper(II) di-n-butyldithiocarbamate, copper(II) di-n-pentyldithiocarbamate, copper(II) di-n-hexyldithiocarbamate, copper(II) di-phenyldithiocarbamate, the methylethyldithiocarbamate of Cu(II), the methyl-n-propyldithiocarbamate of Cu(II), the methyl-n-butyldithiocarbamate of Cu(II), the methyl-n-pentyldithiocarbamate of Cu(II), the methyl-n-hexyldithiocarbamate of Cu(II), the methylphenyldithiocarbamate of Cu(II), the ethyl-n-propyldithiocarbamate of Cu(II), the ethyl-n-butyl-dithiocarbamate of Cu(II), the ethyl-n-pentyldithiocarbamate of Cu(II), the ethyl-n-hexyldithiocarbamate of Cu(II), the ethylphenyldithiocarbamate of Cu(II), the n-propyl-n-butyldithiocarbamate of Cu(II), the n-propyl-n-pentylditihiocarbamate of Cu(II), the n-propyl-n-hexyldithiocarbamate of Cu(II), the n-propylphenyldithiocarbamate of Cu(II), the n-butyl-n-pentyldithiocarbamate of Cu(II), the n-butyl-n-hexyl-dithiocarbamate of Cu(II), the n-butylphenyldithiocarbamate of Cu(II), the n-pentyl-n-hexyldithiocarbamate of Cu(II), the n-pentylphenyldithiocarbamate of Cu(II) and the n-hexylphenyldithiocarbamate of Cu(II), and also the bis(2-hydroxyethyl)dithiocarbamate of Cu(II).

It will be appreciated that the corresponding Cu(I) carbamates, thiocarbamates and dithiocarbamates are also suitable for the inventive procedure. For the inventive procedure, particular preference is given to using the dimethyldithiocarbamate, the diethyldithiocarbamate and the di-n-butyldithiocarbamate of Cu(II). Also suitable for the process according to the invention are mixed salts of copper, such as copper(II) dihydrocarbylthiophosphate or copper(II) dihydrocarbyldithiophosphate.

Based on the molar amount of acrylic acid present in the liquid phase P, in the process according to the invention, the at least one chemical compound of the element copper will be added in such amounts that the copper content G of the liquid phase P, based on the molar amount of acrylic acid present therein, is generally 0.01 mol.-ppm to 5 mol % or to 3 mol %. In other words, G in the process according to the invention may be a 0.05 molar ppm to 2 mol %, or 0.1 molar ppm to 1 mol %, or 1 molar ppm to 5000 molar ppm, or 3 molar ppm to 3000 molar ppm, or 5 molar ppm to 1000 molar ppm, or 10 molar ppm to 800 molar ppm, or molar ppm to 500 molar ppm, or 30 molar ppm to 300 molar ppm, or 40 molar ppm to 200 molar ppm, or 50 molar ppm to 100 molar ppm, or 0.1 molar ppm to 10 molar ppm.

The at least one chemical compound comprising the element copper can be added to the liquid phase P, for example, as a pure substance or preferably in solution. The solvent used may, for example, be liquid phase P itself, or acrylic acid (generally acrylic acid of elevated purity), or that solvent in which the acrylic acid is dissolved in the liquid phase P, or a constituent or a mixture of several constituents of this solvent.

Preferably, in the process according to the invention, solutions of the at least one chemical compound comprising the element Cu in acrylic acid, or in water, or in absorbent into which the acrylic acid has been absorbed from the product gas mixture of the heterogeneously catalyzed partial gas phase oxidation of the $C_3$ precursor compound, are added to the liquid phase P.

Frequently, the liquid phase P in the process according to the invention will comprise at least 20% by weight, or at least 30% by weight, or at least 40% by weight, or at least 50% by weight, or at least 60% by weight, or at least 70% by weight, or at least 80% by weight, or at least 90% by weight, or at least 95% by weight, or at least 98% by weight of acrylic acid (based in each case on the weight of the liquid phase P).

Frequently, the liquid phase P in the process according to the invention will also comprise water. In principle, the water content of the liquid phase P in the process according to the invention may be at least 1% by weight, or at least 5% by weight, or at least 10% by weight, or at least 20% by weight, or at least 30% by weight, or at least 40% by weight, or at least 60% by weight, or at least 80% by weight.

However, the process according to the invention is also relevant especially when the liquid phase P to be treated in accordance with the invention comprises less than 30% by weight, or ≤29% by weight, or ≤27% by weight, or ≤25% by weight, or ≤20% by weight, or ≤15% by weight, or ≤10% by weight, or ≤5% by weight of water (smaller water contents reduce glyoxal hydrate formation). In many cases, the water content of the liquid phase P will, however, be ≥0.1% by weight, or ≥0.5% by weight, or ≥1% by weight (the amounts stated above include the water content of, for example, glyoxal hydrates).

Frequently, the liquid phase P will comprise high-boiling absorbent into which the acrylic acid has been absorbed, for example, from the product gas mixture of the heterogeneously catalyzed partial gas phase oxidation of the $C_3$ precursor compound (cf., for example, DE-A 102009027401).

High-boiling absorbents are understood in this document to mean absorbents whose boiling point at standard pressure is above that of acrylic acid. Normally, the boiling point of the absorbent at standard pressure (1 atm=approx. $10^5$ Pa) is at least 20° C., preferably at least 50° C., more preferably at least 75° C. and most preferably at least 100° C. or at least 125° C. above the boiling point of acrylic acid (141° C. at 1 atm; in contrast to the boiling point of propionic acid of 141.35° C. at the same pressure; cf. WO 2007/074045) at the same pressure. Frequently, the boiling point of aforementioned absorbents at standard pressure is at values of ≤400° C., frequently ≤350° C. and in many cases also ≤300° C. or ≤280° C. In a particularly suitable manner, the boiling point of the absorbent is at values in the range from 200 to 350° C. (based on standard pressure). For example, useful absorbents of this kind are all of those which are recommended in documents DE-A 10336386, DE-A 02449780, DE-A 19627850, DE-A 19810962, DE-A 04308087, EP-A 0722926 and DE-A 04436243, and also DE-A 102009027401.

In general, the high-boiling absorbents are organic liquids. They frequently consist to an extent of at least 70% by weight of those organic molecules which do not have an externally active polar group and are thus incapable, for example, of forming hydrogen bonds. Particularly advantageous absorbents are, for example, diphenyl ether, diphenyl (biphenyl), mixtures, called Diphyl®, of diphenyl ether (70 to 75% by weight) and diphenyl (25 to 30% by weight), and also dimethyl phthalate, diethyl phthalate, and mixtures of Diphyl and dimethyl phthalate or Diphyl and diethyl phthalate, or Diphyl, dimethyl phthalate and diethyl phthalate. A group of mixtures which are particularly suitable for absorption purposes are those composed of 75 to 99.9% by weight of Diphyl and 0.1 to 25% by weight of dimethyl phthalate and/or diethyl phthalate.

High-boiling absorbents in the context of this document may also be ionic liquids.

For example, the liquid phase P in the process according to the invention may comprise at least 1% by weight, or at least 5% by weight, or at least 10% by weight, or at least 20% by weight, or at least 30% by weight, or at least 40% by weight, or at least 60% by weight, or at least 80% by weight of high-boiling absorbent.

While the prior art processes aim to convert acrylic acid to the liquid phase in the presence of vanishingly small amounts of glyoxal, the reason for the appeal of the present procedure is not least because elevated glyoxal contents in liquid phases P in the inventive procedure, with regard to the tendency of the acrylic acid likewise present therein to unwanted free-radical polymerization, are no longer found to be disadvantageous, but instead advantageous.

In other words, the inventive procedure displays its advantageous action especially when the liquid phase P, based on the weight of the acrylic acid present therein, is at least 150 ppm by weight, or at least 175 ppm by weight, or at least 200 ppm by weight, or at least 225 ppm by weight, or at least 250 ppm by weight, or at least 275 ppm by weight, or at least 300 ppm by weight of glyoxal. The process according to the invention is thus also suitable when the glyoxal content of the liquid phase P on the same basis is ≥325 ppm by weight, or ≥350 ppm by weight, or ≥375 ppm by weight, or 400 ppm by weight, or ≥450 ppm by weight, or ≥500 ppm by weight, or ≥550 ppm by weight, or ≥600 ppm by weight, or ≥700 ppm by weight, or ≥800 ppm by weight, or ≥1000 ppm by weight, or ≥1250 ppm by weight, or ≥1500 ppm by weight, or ≥2000 ppm by weight, or ≥2500 ppm by weight.

Normally, the glyoxal contents of the liquid phase P on the basis as described above will be ≤5% by weight, frequently ≤4% by weight or ≤3% by weight, often also ≤2% by weight or ≤1% by weight.

In all aforementioned cases, the propionic acid content in the liquid phase P on a corresponding basis (based on the weight of acrylic acid present) may simultaneously be ≥150 ppm by weight, or ≥175 ppm by weight, or ≥200 ppm by weight, or ≥225 ppm by weight, or ≥250 ppm by weight, or ≥275 ppm by weight, or ≥300 ppm by weight, or ≥325 ppm by weight, or ≥350 ppm by weight, or ≥375 ppm by weight, or ≥400 ppm by weight, or ≥450 ppm by weight, or ≥500 ppm by weight, or ≥550 ppm by weight, or ≥600 ppm by weight, or ≥700 ppm by weight, or ≥800 ppm by weight, or ≥1000 ppm by weight, or ≥1250 ppm by weight, or ≥1500 ppm by weight, or ≥2000 ppm by weight, or ≥2500 ppm by weight.

Normally, in all aforementioned cases, the propionic acid contents of the liquid phase P on the basis as described above will be ≤5% by weight, frequently ≤4% by weight or ≤3% by weight, often ≤2% by weight, or ≤1% by weight.

It will be appreciated that the liquid phase P may comprise, as well as glyoxal and propionic acid, as further secondary components and typical secondary reaction products of the heterogeneously catalyzed partial gas phase oxidation of a $C_3$ precursor compound to acrylic acid, compounds such as formaldehyde, acrolein, crotonaldehyde, furfurals (e.g. furfural-3, furfural-2), benzaldehyde, propionaldehyde, protoanemonine, allyl acrylate, formic acid, acetic acid, maleic acid, benzoic acid and/or maleic anhydride (for example in proportions as detailed in WO 2006/002713, WO 2008/090190, DE-A 10 2007 004960 and DE-A 10 2009 027401, especially in the different liquid substance mixtures of the working examples thereof).

As already mentioned, it is frequently necessary for liquid phases P for treatment in accordance with the invention to be stored over a prolonged period. During this period, the acrylic acid reacts with itself to a certain extent, and Michael addition forms limited amounts of diacrylic acid (c.f., for example, WO 98/01414 and WO 2005/035478).

The process according to the invention is therefore suitable especially for liquid phases P which, based on the weight of the acrylic acid present in the liquid phase P, in addition to the amounts of glyoxal, propionic acid and acrylic acid already stated, additionally also comprise ≥100 ppm by weight, or ≥150 ppm by weight, or ≥200 ppm by weight, or ≥250 ppm by weight, or ≥300 ppm by weight, or ≥350 ppm by weight, or ≥400 ppm by weight, or ≥450 ppm by weight, or ≥500 ppm by weight, or ≥600 ppm by weight, or ≥800 ppm by weight, or ≥1000 ppm by weight, or ≥1250 ppm by weight, or ≥1500 ppm by weight, or ≥1750 ppm by weight, or ≥2000 ppm by weight, or ≥2500 ppm by weight, or ≥3000 ppm by weight, or ≥4000 ppm by weight, or ≥5000 ppm by weight, or ≥7500 ppm by weight, or ≥10 000 ppm by weight of diacrylic acid.

In general, the diacrylic acid content of liquid phases P to be treated in accordance with the invention, based on the weight of the acrylic acid present therein, will be not more than 20% by weight, frequently not more than 15% by weight or not more than 10% by weight, and in many cases not more than 5% by weight.

Elevated diacrylic acid contents of the liquid phases P to be treated in accordance with the invention are not disadvantageous in that diacrylic acid itself has inhibiting action with respect to acrylic acid (cf. WO 2005/035478, R. C. Lamb et al., J. Am. Chem. Soc. (85), 1963, pp. 3483-3486 and "Polymerisationsinhibierung von (Meth)Acrylaten, thesis by Dipl.-lng. Holger Becker, Technische Universität Darmstadt, 2003") and can be redissociated to acrylic acid by employment and/or the action of elevated temperature on completion of removal.

Diacrylic acid contents of liquid phases P can be determined in a simple manner by means of high-resolution $^1H$ NMR (cf. "Polymerisationsinhibierung von (Meth-)Acrylaten, thesis by Dipl.-lng. Holger Becker, Technische Universität Darmstadt, 2003"). The method evaluates the specific signal shape and signal position, and also signal area, of the relevant $^1H$ resonance lines. The propionic acid contents of liquid phases P are generally determined by gas chromatography. Their acrylic acid contents can likewise be determined by $^1H$ NMR, by gas chromatography or by HPLC.

The process according to the invention is suitable for inhibiting unwanted free-radical polymerization of acrylic acid present in a liquid phase P both during the storage thereof and during the handling thereof for processing purposes.

The latter case is present especially when the liquid phase P is subjected to a noncrystallizative thermal separating process (the temperatures which occur are generally above 50° C., usually above 60° C. or 70° C., or above 90° C. or 110° C.). These are generally those thermal separating processes in which gaseous (ascending) and liquid (descending) streams or two liquid streams are conducted in countercurrent in separating columns comprising separating internals, and heat and mass transfer takes place as a result of the gradients which exist between the streams, which ultimately causes the separating action desired in the separating column. Examples of such noncrystallizative thermal separating processes are rectification, azeotropic rectification, extraction, desorption, stripping, distillation, azeotropic distillation and adsorption. Since liquid phases P to be treated in accordance with the invention arise not least when the product gas mixture of the heterogeneously catalyzed partial gas phase oxidation of a $C_3$ precursor compound to acrylic acid is subjected to an absorption, or a fractional condensation, or a partial condensation for basic removal of acrylic acid from the product gas mixture, the process according to the invention is also suitable for inhibiting polymerization of liquid phases P which occur in the course of such thermal separating processes. Of course, the process according to the invention for inhibiting polymerization is also suitable when the liquid phase P is subjected to a crystallizative thermal separating process.

The term "thermal separating process" is supposed to express that heat has to be supplied to or removed from the system to achieve the desired separating action (cf. DE-A 10 2008 041573 and DE-A 10 2008 8040799).

The at least one chemical compound of the element copper to be added in accordance with the invention may be added to the liquid phase P to be treated for processing purposes as early as the start of the thermal separating process (i.e. it may be supplied to the thermal process having already been treated in accordance with the invention). It will be appreciated that the at least one chemical compound of the element copper may also be added only in the course of the thermal separating process (for example, in a rectification dissolved in the return liquid, or in an absorption dissolved in the absorbent, or in a fractional condensation dissolved in the return liquid, or in a direct cooling of the product gas mixture of the heterogeneously catalyzed partial gas phase oxidation of the $C_3$ precursor compound dissolved in the quench liquid used for direct cooling).

It will be appreciated that the at least one chemical compound of the element copper to be added in accordance with the invention to the liquid phase P need not be the only inhibitor system added to the liquid phase P. Instead, the liquid phase P may additionally comprise one or more added inhibitors from the group comprising the nitroxyl radicals (also known as N-oxyl radicals) (for example those disclosed in DE-A 19734171, such as 4-hydroxy-2,2,6,6-tetramethylpiperidine 1-oxyl or 1,4-dihydroxy-2,2,6,6,-tetramethylpiperidine), phenothiazines, for example dibenzo-1,4-thiazine (phenothiazine), phenolic compounds such as hydroquinone, 2,4-dimethyl-6-t-butylphenol and hydroquinone monomethyl ether, molecular oxygen, cerium salts, for example cerium(III) salts, manganese salts (e.g. manganese(III) salts such as manganese(III) acetate dihydrate and manganese(III) di-n-butyldithiocarbamate, p-phenylenediamines (for example those disclosed in DE-A 19734171), organic nitroso compounds such as 4-nitrosophenol (and the others disclosed in DE-A 19734171), methylene blue and all other inhibitors disclosed, for example, in EP-A 765856. The aforementioned inhibitors may be added to the liquid phase P in appropriate amounts, as detailed and recommended in this document for the at least one copper-comprising compound to be added to the liquid phase P.

In the case of performance of noncrystallizative thermal separating processes on liquid phases P treated in accordance with the invention in separating columns comprising installed separating internals (e.g. trays such as dual-flow trays), as an additional inhibiting measure, for example, air or nitrogen-enriched air (lean air) as a source for molecular oxygen can be flowed through the separating column (e.g. a rectification column or absorption column), as practiced, for example, in DE-A 102009027401 or in DE-A 102007004960.

Such thermal separating processes (e.g. all thermal separating processes described in WO 2011/000808 A2, DE-A 10336386, DE-A 19924532, DE-A 19924533, and DE-A 102007004960) are carried out according to the invention preferably in apparatus conforming to the recommendations of U.S. Pat. No. 6,441,228 B2 and U.S. Pat. No. 6,966,973 B2.

A favorable inhibiting combination for stabilization of the rectification, detailed in DE A 102009027401, of the acrylic acid-comprising absorbate A* in the rectification column K30 comprises (in addition to the air which flows through the rectification column K30), based on the amount of acrylic acid to be stabilized (to be inhibited) in each case, for example, 0.1 to 3 molar ppm of Cu (added in the form of at least one Cu-comprising compound (preferably Cu(II) di-n-butyldithiocarbamate) and 50 to 1000 ppm by weight of phenothiazine, preferably 0.2 to 2 molar ppm, of Cu, and 100 to 500 ppm by weight of phenothiazine, and more preferably 0.3 to 1 molar ppm of Cu and 200 to 400 ppm by weight of phenothiazine. The inhibitor is advantageously supplied to the rectification column K30 via the return liquid, dissolved therein, and via the absorbate A* supplied to the rectification column K30, dissolved therein.

One advantage of the inventive procedure is, as already stated, that there is no need to proceed from high-purity $C_3$ precursor compounds of acrylic acid on the route to production of a liquid phase P in the heterogeneously catalyzed partial gas phase oxidation of a $C_3$ precursor compound of acrylic acid.

For example, for the heterogeneously catalyzed partial gas phase oxidation to prepare acrylic acid, it is possible to use a starting reaction gas mixture which comprises, based on the molar amount of the $C_3$ precursor compound used and present therein (e.g. propane, propylene, acrolein, propionic acid, propionaldehyde, propanol and/or glycerol, among which propylene and acrolein are preferred), comprises a molar total amount of $C_2$ compounds (e.g. ethane, ethylene, acetylene, acetaldehyde, acetic acid and/or ethanol) of ≥100 molar ppm, or ≥150 molar ppm, or ≥200 molar ppm, or ≥250 molar ppm, or ≥300 molar ppm, or ≥350 molar ppm, or ≥400 molar ppm, or ≥450 molar ppm, or ≥500 molar ppm, or ≥600 molar ppm, or ≥750 molar ppm, or ≥1000 molar ppm, or ≥1250 molar ppm, or ≥1500 molar ppm, or ≥2000 molar ppm, or ≥2500 molar ppm, or ≥3000 molar ppm. In general, the aforementioned total molar amount of $C_2$ compounds in the starting reaction gas mixture of the heterogeneously catalyzed partial gas phase oxidation of the $C_3$ precursor compound to acrylic acid (on the same basis) will not be more than 30 mol %, usually not more than 20 mol % or than 10 mol %, frequently not more than 5 mol %.

In addition, for the heterogeneously catalyzed partial gas phase oxidation to prepare acrylic acid, on the route to the preparation of the liquid phase P, it is possible to use a starting reaction gas mixture which, based on the amount of the $C_3$ precursor compound used and present therein (e.g. propane, propylene, acrolein, propionic acid, propionaldehyde, propanol, and/or glycerol, among which propylene and acrolein are preferred), in addition to the aforementioned total amounts of $C_2$ compounds, may comprise a total molar amount of cyclopropane of ≥10 molar ppb (ppm=parts per million; ppb=parts per billion), or ≥25 molar ppb, or ≥50 molar ppb, or ≥75 molar ppb, or ≥100 molar ppb, or ≥1 molar ppm, or ≥10 molar ppm, or ≥20 molar ppm, or ≥30 molar ppm, or ≥50 molar ppm, or ≥75 molar ppm, or ≥100 molar ppm, or ≥150 molar ppm, or ≥250 molar ppm, or ≥300 molar ppm, or ≥400 molar ppm, or ≥500 molar ppm, or ≥750 molar ppm, or ≥1000 molar ppm, or ≥1500 molar ppm, or ≥2000 molar ppm of cyclopropane. In general, the cyclopropane contents of the starting reaction gas mixture for the heterogeneously catalyzed partial gas phase oxidation of the $C_3$ precursor compounds to acrylic acid, on the above basis, will not be more than 5 mol %, frequently not more than 3 mol % or than 2 mol % and in many cases not more than 1 mol %.

In addition, the starting reaction gas mixture used for the heterogeneously catalyzed partial gas phase oxidation to prepare acrylic acid may, for example in the case of propylene or acrolein as the $C_3$ precursor compound (but also in the case of the other $C_3$ precursor compounds other than n-propane), based on the weight of the propylene or acrolein present (of the $C_3$ precursor compound other than n-propane), may comprise ≥0.05% by weight of n-propane, or ≥0.1% by weight of n-propane, or ≥0.2% by weight of n-propane, or ≥0.3% by weight of n-propane, or ≥0.4% by weight of n-propane, or ≥0.5% by weight of n-propane, or ≥0.75% by weight of n-propane, or ≥1% by weight of n-propane, or ≥2% by weight of n-propane, or ≥3% by weight of n-propane, or ≥5% by weight of n-propane, or ≥6% by weight of n-propane, or ≥10% by weight of n-propane, or ≥20% by weight of n-propane. Typically, the starting reaction gas mixture of a heterogeneously catalyzed partial gas phase oxidation of propylene and/or acrolein (of the $C_3$ precursor compound other than n-propane) to acrylic acid will, however, not be more than 80% by volume, frequently not more than 70% by volume and in many cases not more than 60% by volume (but usually not less than 0.1% by volume) of n-propane.

The term "starting reaction gas mixture" in all aforementioned cases means that gas mixture which is supplied to the catalyst bed for the purpose of partial oxidation of the $C_3$ precursor compound present therein to acrylic acid. In addition to the $C_3$ precursor compound, unwanted impurities and molecular oxygen as an oxidizing agent, the starting reaction gas mixture generally also comprises inert diluent gases, for example $N_2$, $CO_2$, $H_2O$, noble gas, molecular hydrogen, etc. Each inert diluent gas is normally such that at least 95 mol % of the starting amount thereof remains unchanged in the course of the heterogeneously catalyzed partial oxidation.

The proportion of the $C_3$ precursor compound in the starting reaction gas mixture may, for example, be in the range from 4 to 20% by volume, or from 5 to 15% by volume, or from 6 to 12% by volume.

Normally, the starting reaction gas mixture comprises, based on the stoichiometry of the partial oxidation reaction of the $C_3$ precursor compounds to acrylic acid, an excess of molecular oxygen, in order to reoxidize the generally oxidic catalysts again.

In the case of a subsequent application of the inventive procedure, this excess may be selected at a particularly high level, since increasing oxygen excess is generally also accompanied by an increase in unwanted formation of the secondary component glyoxal.

In the same way, in the heterogeneously catalyzed partial gas phase oxidation of the $C_3$ precursor compound to acrylic acid, the maximum reaction temperature present in the catalyst bed can be selected at a comparatively elevated level when the process according to the invention is employed after the partial oxidation. One reason for this is that increasing maximum temperature is generally also accompanied by an increase in unwanted formation of the secondary component glyoxal. However, the employment of elevated maximum temperatures generally permits the use of catalysts with relatively low activity, which opens up the possibility of prolonged catalyst service life. However, in the case of use of catalysts with relatively low activity, increasing conversion of the $C_3$ precursor compound frequently also goes hand in hand, to an increasing degree, with unwanted full combustion thereof. An intermediate formed in this case may likewise optionally be glyoxal.

In a similar manner, in the context of the inventive procedure, it is also possible to proceed more generously in the selection of the space velocity of $C_3$ precursor compound on the catalyst bed.

In addition, it has been found that glyoxal by-product formation is promoted by elevated steam contents in the reaction gas mixture. The process according to the invention is therefore of relevance not least when the starting reaction gas mixture used for the heterogeneously catalyzed partial gas phase oxidation of the $C_3$ precursor compound comprises ≥1% by weight, or ≥2% by weight, or ≥3% by weight, or ≥4% by weight, or ≥5% by weight, or ≥7% by weight, or ≥9% by weight, or ≥15% by weight, or ≥20% by weight of steam. In general, the steam content of the starting reaction gas mixture will, however, not be more than 40% by weight, frequently not more than 30% by weight.

Otherwise, the process for heterogeneously catalyzed partial gas phase oxidation to prepare acrylic acid can be performed in a manner known per se as described in the prior art.

When the $C_3$ precursor compound is, for example, propylene and/or acrolein, the heterogeneously catalyzed partial gas phase oxidation can be performed, for example, as described in documents WO 2005/042459, WO 2005/047224 and WO 2005/047226.

When the $C_3$ precursor compound is, for example, propane, the heterogeneously catalyzed partial gas oxidation to prepare acrylic acid can be performed, for example, as described in documents EP-A 608 838, DE-A 198 35 247, DE-A 102 45 585 and DE-A 102 46 119.

When the $C_3$ precursor compound is, for example, glycerol, the heterogeneously catalyzed partial gas phase oxidation to prepare acrylic acid can be performed, for example, as described in documents WO 2007/090991, WO 2006/114506, WO 2005/073160, WO 2006/114506, WO 2006/092272 or WO 2005/073160.

It has also already been proposed to obtain the propylene as the $C_3$ precursor compound by a partial dehydrogenation and/or oxydehydrogenation of propane, upstream of the partial gas phase oxidation (e.g. WO 076370, WO 01/96271, EP-A 117146, WO 03/011804 and WO 01/96270).

The process according to the invention can especially also be employed advantageously when the glyoxal present in the liquid phase P is present to an extent of at least 20 mol %, or to an extent of at least 30 mol %, or to an extent of at least 50 mol %, or to an extent of at least 70 mol %, or to an extent of at least 90 mol %, or to an extent of at least 95 mol % as monomeric glyoxal monohydrate and/or monomeric glyoxal dihydrate in the liquid phase P.

The process according to the invention is favorable not least when the liquid phase P to be treated in accordance with the invention originates from a product gas mixture of a heterogeneously catalyzed partial gas phase oxidation of a $C_3$ precursor of acrylic acid which, based on the molar amount of acrylic acid present in the product gas mixture, comprises at least 100, or at least 150, or at least 200 molar ppm of glyoxal, or ≥250 molar ppm of glyoxal, or ≥300 molar ppm of glyoxal, or ≥400 molar ppm of glyoxal, or ≥500 molar ppm of glyoxal, or ≥750 molar ppm of glyoxal, or ≥1000 molar ppm of glyoxal, or ≥1250 molar ppm of glyoxal, or ≥1500 molar ppm of glyoxal (to determine the aforementioned glyoxal contents of the product gas mixture based on the molar amount of acrylic acid present, by cooling the latter, at least the acrylic acid present therein, the hemiacetals and/or acetals of glyoxal present therein, and the monomeric glyoxal present therein will be converted to the condensed phase and the latter will be analyzed for its content of glyoxal and acrylic acid as soon as possible after production thereof as described in this document for a liquid phase P).

This is true in particular when the product gas mixture simultaneously has propionic acid contents corresponding to the aforementioned proportions.

Normally, the aforementioned propionic acid and glyoxal contents of the product gas mixture (on the same basis) will be ≤5 mol %. In many cases, the acrylic acid content of the aforementioned product gas mixtures will be 1 to 30% by volume.

Frequently, liquid phases P to be treated in accordance with the invention are also subjected to an azeotropic rectification to remove water present therein. Suitable entraining agents in this regard include especially heptane, dimethylcyclohexane, ethylcyclohexane, toluene, ethylbenzene, octane, chlorobenzene, xylene or mixtures thereof (for example 60% by weight of toluene and 40% by weight of heptane). As alternative entraining agents, it is also possible to use methyl isobutyl ketone or isopropyl acetate. Otherwise, the procedure may be as described in documents EP-A 778255, EP-A 695736 and US 2004/0242826. Liquid phases P to be treated in accordance with the invention are therefore especially also those liquid phases P which comprise at least one of the aforementioned entraining agents and water. In general, the water content of such liquid phases P is at least 10% by weight, and the content of azeotropic entraining agent is at least 1% by weight, frequently at least 2% by weight or at least 5% by weight.

The process according to the invention is also relevant not least when glyoxal and propionic acid present in a liquid phase P treated in accordance with the invention are removed therefrom by crystallization, in which case the glyoxal and the propionic acid are enriched in the remaining mother liquor and the acrylic acid in the crystals, and the mother liquor is recycled into at least one of the process steps with the aid of which the liquid phase P treated in accordance with the invention has been obtained (prepared) from the product gas mixture of the heterogeneously catalyzed partial gas phase oxidation of the $C_3$ precursor compound. The crystallizative removal process can be performed in a corresponding manner, as described in documents DE-A 102008041573, DE-A 102008040799 and WO 2007/074044, and also DE-A 102007029053.

Corrosion studies have shown that, for liquid phases P inhibited in accordance with the invention with at least one chemical compound comprising the element Cu, DIN material 1.4571 is a suitable apparatus material having entirely satisfactory corrosion resistance.

The present patent application thus comprises especially the following inventive embodiments:

1. A process for inhibiting unwanted free-radical polymerization of acrylic acid present in a liquid phase P and whose acrylic acid content is at least 10% by weight and which, based on the weight of the acrylic acid present therein, additionally comprises at least 100 ppm by weight of glyoxal, wherein at least one chemical compound of the element copper is added to the liquid phase P.
2. The process according to embodiment 1, wherein the at least one chemical compound has the copper in the oxidation state +2.
3. The process according to embodiment 1, wherein the at least one chemical compound has the copper in the oxidation state +1.
4. The process according to any of embodiments 1 to 3, wherein the at least one chemical compound of the element copper is added in such an amount that the liquid phase P, based on the molar amount of acrylic acid present therein, comprises 0.01 molar ppm to 5 mol % or 0.01 molar ppm to 3 mol % of Cu.
5. The process according to any of embodiments 1 to 4, wherein the at least one chemical compound of the element copper is added in such an amount that the liquid phase P, based on the molar amount of acrylic acid present therein, comprises 0.05 molar ppm to 2 mol % of Cu.
6. The process according to any of embodiments 1 to 5, wherein the at least one chemical compound of the element copper is added in such an amount that the liquid phase P, based on the molar amount of acrylic acid present therein, comprises 0.1 molar ppm to 1 mol % of Cu.
7. The process according to any of embodiments 1 to 6, wherein the at least one chemical compound of the element copper is added in such an amount that the liquid phase P, based on the molar amount of acrylic acid present therein, comprises 1 molar ppm to 5000 molar ppm of Cu.
8. The process according to any of embodiments 1 to 7, wherein the at least one chemical compound of the element copper is added in such an amount that the liquid phase P, based on the molar amount of acrylic acid present therein, comprises 3 molar ppm to 3000 molar ppm of Cu.
9. The process according to any of embodiments 1 to 8, wherein the at least one chemical compound of the element copper is added in such an amount that the liquid phase P, based on the molar amount of acrylic acid present therein, comprises 5 molar ppm to 1000 molar ppm of Cu.
10. The process according to any of embodiments 1 to 9, wherein the at least one chemical compound of the element copper is added in such an amount that the liquid phase P, based on the molar amount of acrylic acid present therein, comprises 20 molar ppm to 500 molar ppm of Cu.
11. The process according to any of embodiments 1 to 6, wherein the at least one chemical compound of the element copper is added in such an amount that the liquid phase P, based on the molar amount of acrylic acid present therein, comprises 0.1 molar ppm to 10 molar ppm of Cu.
12. The process according to any of embodiments 1 to 11, wherein the at least one chemical compound of the element copper added to the liquid phase P is dispersed in the liquid phase P and/or dissolved in the liquid phase P.
13. The process according to any of embodiments 1 to 12, wherein the acrylic acid content of the liquid phase P is at least 20% by weight.
14. The process according to any of embodiments 1 to 13, wherein the acrylic acid content of the liquid phase P is at least 40% by weight.
15. The process according to any of embodiments 1 to 14, wherein the acrylic acid content of the liquid phase P is at least 60% by weight.
16. The process according to any of embodiments 1 to 15, wherein the acrylic acid content of the liquid phase P is at least 80% by weight.
17. The process according to any of embodiments 1 to 16, wherein the acrylic acid content of the liquid phase P is at least 90% by weight.
18. The process according to any of embodiments 1 to 17, wherein the liquid phase P comprises at least one 1% by weight of water.
19. The process according to any of embodiments 1 to 18, wherein the liquid phase P comprises at least one 5% by weight of water.
20. The process according to any of embodiments 1 to 15, wherein the liquid phase P comprises ≤29% by weight of water.
21. The process according to any of embodiments 1 to 15, wherein the liquid phase P comprises ≤27% by weight of water.
22. The process according to any of embodiments 1 to 15, wherein the liquid phase P comprises ≤25% by weight of water.
23. The process according to any of embodiments 1 to 15, wherein the liquid phase P comprises ≤20% by weight of water.
24. The process according to any of embodiments 1 to 15, wherein the liquid phase P comprises ≤10% by weight of water.

25. The process according to any of embodiments 20 to 24, wherein the liquid phase P comprises ≥0.1% by weight of water.
26. The process according to any of embodiments 1 to 12, wherein the liquid phase P comprises at least 10% by weight of a high-boiling organic solvent whose boiling point at a pressure of $10^5$ Pa is at least 20° C. above the boiling point of acrylic acid at the same pressure.
27. The process according to embodiment 26, wherein the liquid phase P comprises at least 30% by weight of the high-boiling organic solvent.
28. The process according to embodiment 26, wherein the liquid phase P comprises at least 60% by weight of the high-boiling organic solvent.
29. The process according to any of embodiments 26 to 28, wherein the high-boiling organic solvent comprises at least one of the solvents diphenyl ether, diphenyl, dimethyl phthalate and diethyl phthalate.
30. The process according to any of embodiments 1 to 25, wherein the liquid phase P comprises at least one of the azeotropic entraining agents heptane, dimethylcyclohexane, ethylcyclohexane, toluene, ethylbenzene, octane, chlorobenzene, xylene, methyl isobutyl ketone and isopropyl acetate.
31. The process according to embodiment 30, wherein the liquid phase P comprises at least 1% by weight of the at least one azeotropic entraining agent.
32. The process according to any of embodiments 1 to 31, wherein the liquid phase P, based on the weight of the acrylic acid present therein, comprises at least 150 ppm by weight of glyoxal.
33. The process according to any of embodiments 1 to 31, wherein the liquid phase P, based on the weight of the acrylic acid present therein, comprises at least 200 ppm by weight of glyoxal.
34. The process according to any of embodiments 1 to 31, wherein the liquid phase P, based on the weight of the acrylic acid present therein, comprises at least 250 ppm by weight of glyoxal.
35. The process according to any of embodiments 1 to 31, wherein the liquid phase P, based on the weight of the acrylic acid present therein, comprises at least 300 ppm by weight of glyoxal.
36. The process according to any of embodiments 1 to 31, wherein the liquid phase P, based on the weight of the acrylic acid present therein, comprises at least 350 ppm by weight of glyoxal.
37. The process according to any of embodiments 1 to 31, wherein the liquid phase P, based on the weight of the acrylic acid present therein, comprises at least 400 ppm by weight of glyoxal.
38. The process according to any of embodiments 1 to 37, wherein the liquid phase P, based on the weight of the acrylic acid present therein, comprises ≤5% by weight of glyoxal.
39. The process according to any of embodiments 1 to 38, wherein the liquid phase P, based on the weight of the acrylic acid present therein, comprises ≤3% by weight of glyoxal.
40. The process according to any of embodiments 1 to 39, wherein the liquid phase P, based on the weight of the acrylic acid present therein, comprises ≥150 ppm by weight of propionic acid.
41. The process according to any of embodiments 1 to 39, wherein the liquid phase P, based on the weight of the acrylic acid present therein, comprises ≥175 ppm by weight of propionic acid.
42. The process according to any of embodiments 1 to 39, wherein the liquid phase P, based on the weight of the acrylic acid present therein, comprises ≥200 ppm by weight of propionic acid.
43. The process according to any of embodiments 1 to 39, wherein the liquid phase P, based on the weight of the acrylic acid present therein, comprises ≥225 ppm by weight of propionic acid.
44. The process according to any of embodiments 1 to 39, wherein the liquid phase P, based on the weight of the acrylic acid present therein, comprises ≥250 ppm by weight of propionic acid.
45. The process according to any of embodiments 1 to 39, wherein the liquid phase P, based on the weight of the acrylic acid present therein, comprises ≥275 ppm by weight of propionic acid.
46. The process according to any of embodiments 1 to 39, wherein the liquid phase P, based on the weight of the acrylic acid present therein, comprises ≥300 ppm by weight of propionic acid.
47. The process according to any of embodiments 1 to 39, wherein the liquid phase P, based on the weight of the acrylic acid present therein, comprises ≥350 ppm by weight of propionic acid.
48. The process according to any of embodiments 1 to 39, wherein the liquid phase P, based on the weight of the acrylic acid present therein, comprises ≥400 ppm by weight of propionic acid.
49. The process according to any of embodiments 1 to 39, wherein the liquid phase P, based on the weight of the acrylic acid present therein, comprises ≥500 ppm by weight of propionic acid.
50. The process according to any of embodiments 1 to 39, wherein the liquid phase P, based on the weight of the acrylic acid present therein, comprises ≥600 ppm by weight of propionic acid.
51. The process according to any of embodiments 1 to 50, wherein the liquid phase P, based on the weight of the acrylic acid present therein, comprises ≥5% by weight of propionic acid.
52. The process according to any of embodiments 1 to 51, wherein the liquid phase P, based on the weight of the acrylic acid present therein, comprises ≥4% by weight of propionic acid.
53. The process according to any of embodiments 1 to 52, wherein the liquid phase P, based on the weight of the acrylic acid present therein, comprises ≥100 ppm by weight of diacrylic acid.
54. The process according to any of embodiments 1 to 52, wherein the liquid phase P, based on the weight of the acrylic acid present therein, comprises ≥150 ppm by weight of diacrylic acid.
55. The process according to any of embodiments 1 to 52, wherein the liquid phase P, based on the weight of the acrylic acid present therein, comprises ≥200 ppm by weight of diacrylic acid.
56. The process according to any of embodiments 1 to 52, wherein the liquid phase P, based on the weight of the acrylic acid present therein, comprises ≥250 ppm by weight of diacrylic acid.
57. The process according to any of embodiments 1 to 52, wherein the liquid phase P, based on the weight of the acrylic acid present therein, comprises ≥300 ppm by weight of diacrylic acid.

58. The process according to any of embodiments 1 to 52, wherein the liquid phase P, based on the weight of the acrylic acid present therein, comprises ≥350 ppm by weight of diacrylic acid.

59. The process according to any of embodiments 1 to 52, wherein the liquid phase P, based on the weight of the acrylic acid present therein, comprises ≥400 ppm by weight of diacrylic acid.

60. The process according to any of embodiments 1 to 52, wherein the liquid phase P, based on the weight of the acrylic acid present therein, comprises ≥500 ppm by weight of diacrylic acid.

61. The process according to any of embodiments 1 to 52, wherein the liquid phase P, based on the weight of the acrylic acid present therein, comprises ≥600 ppm by weight of diacrylic acid.

62. The process according to any of embodiments 1 to 52, wherein the liquid phase P, based on the weight of the acrylic acid present therein, comprises ≥700 ppm by weight of diacrylic acid.

63. The process according to any of embodiments 1 to 52, wherein the liquid phase P, based on the weight of the acrylic acid present therein, comprises ≥800 ppm by weight of diacrylic acid.

64. The process according to any of embodiments 1 to 63, wherein the liquid phase P, based on the weight of the acrylic acid present therein, comprises ≤20% by weight of diacrylic acid.

65. The process according to any of embodiments 1 to 64, wherein the liquid phase P, based on the weight of the acrylic acid present therein, comprises ≤10% by weight of diacrylic acid.

66. The process according to any of embodiments 1 to 64, wherein the liquid phase P, based on the weight of the acrylic acid present therein, comprises ≤5% by weight of diacrylic acid.

67. The process according to embodiments 1 to 66, wherein the liquid phase P comprises at least one further compound among the compounds formaldehyde, acrolein, crotonaldehyde, furfural-3, furfural-2, benzaldehyde, propionaldehyde, protoanemonine, allyl acrylate, formic acid, acetic acid, maleic acid, benzoic acid and maleic anhydride.

68. The process according to any of embodiments 1 to 67, wherein the acrylic acid present in the liquid phase P is the product of a heterogeneously catalyzed partial oxidation of a $C_3$ precursor compound of acrylic acid, in which the starting reaction gas mixture which is used for the partial oxidation and comprises the $C_3$ precursor compound, based on the molar amount of the $C_3$ precursor compound present therein, has a total molar amount of $C_2$ compounds (of compounds comprising 2 carbon atoms) of ≥100 molar ppm.

69. The process according to embodiment 68, wherein the total molar amount of $C_2$ compounds is ≥150 molar ppm.

70. The process according to embodiment 68, wherein the total molar amount of $C_2$ compounds is ≥200 molar ppm.

71. The process according to embodiment 68, wherein the total molar amount of $C_2$ compounds is ≤30 mol %, or ≤20 mol %, or ≤10 mol %.

72. The process according to any of embodiments 1 to 71, wherein the acrylic acid present in the liquid phase P is the product of a heterogeneously catalyzed partial oxidation of a $C_3$ precursor compound of acrylic acid, in which the starting reaction gas mixture which is used for the partial oxidation and comprises the $C_3$ precursor compound, based on the molar amount of the $C_3$ precursor compound present therein, has a total molar amount of cyclopropane of ≥10 molar ppb.

73. The process according to embodiment 72, wherein the total molar amount of cyclopropane is ≥50 molar ppb.

74. The process according to embodiment 72, wherein the total molar amount of cyclopropane is ≥1 molar ppm.

75. The process according to embodiment 72, wherein the total molar amount of cyclopropane is ≥10 molar ppm.

76. The process according to embodiment 72, wherein the total molar amount of cyclopropane is ≤3 mol %.

77. The process according to any of embodiments 1 to 76, wherein the acrylic acid present in the liquid phase P is the product of a heterogeneously catalyzed partial oxidation of a $C_3$ precursor compound of acrylic acid, in which the starting reaction gas mixture which is used for the partial oxidation and comprises the $C_3$ precursor compound, based on the weight of the $C_3$ precursor compound other than n-propane present therein, comprises 0.05% by weight of n-propane.

78. The process according to embodiment 77, wherein the starting reaction gas mixture, based on the weight of the $C_3$ precursor compound other than n-propane present therein, comprises ≥0.1% by weight of n-propane.

79. The process according to embodiment 77, wherein the starting reaction gas mixture, based on the weight of the $C_3$ precursor compound other than n-propane present therein, comprises ≥0.3% by weight of n-propane.

80. The process according to embodiment 77, wherein the starting reaction gas mixture, based on the weight of the $C_3$ precursor compound other than n-propane present therein, comprises ≥0.5% by weight of n-propane.

81. The process according to any of embodiments 1 to 80, wherein the acrylic acid present in the liquid phase P is the product of a heterogeneously catalyzed partial oxidation of a $C_3$ precursor compound of acrylic acid, in which the starting reaction gas mixture, which is used for the partial oxidation and comprises the $C_3$ precursor compound, comprises up to 80% by volume, or up to 70% by volume, or up to 60% by volume, of n-propane.

82. The process according to any of embodiments 68 to 81, wherein the $C_3$ precursor compound is propylene, acrolein or n-propane.

83. The process according to any of embodiments 1 to 82, wherein the at least one chemical compound of the element copper is at least one chemical compound from the group consisting of copper(II) phenoxide, copper(II) acetyl acetonate, copper(II) gluconate, copper(II) tartrate, copper (II) acetate, copper(II) formate, copper(II) nitrate, copper (II) hydroxide, copper(II) sulfate, copper(II) carbonate, copper(II) naphthenate, copper(II) acrylate, copper(II) chloride, copper(II) salicylate, copper(II) sulfonate, copper(II) propionate, copper(II) octanoate, copper(II) salts of carbamic acid and the N-substituted derivatives thereof, copper(II) salts of thiocarbamic acid and the N-substituted derivatives thereof, copper(II) salts of dithiocarbamic acid and the N-substituted derivatives thereof, CuCl, CuCN, CuI, CuBr, $Cu_2SO_4$, $Cu_2O$, CuCN and the hydrates of the compounds mentioned.

84. The process according to any of embodiments 1 to 82, wherein the at least one chemical compound of the element copper is at least one chemical compound from the group consisting of copper(II) dimethyldithiocarbamate, copper (II) diethyldithiocarbamate, copper(II) di-n-propyldithiocarbamate, copper(II) di-n-butyldithiocarbamate, copper (II) di-n-pentyldithiocarbamate, copper(II) di-n-hexyldithiocarbamate, copper(II)

di-phenyldithiocarbamate, the methylethyldithiocarbamate of Cu(II), the methyl-n-propyldithiocarbamate of Cu(II), the methyl-n-butyldithiocarbamate of Cu(II), the methyl-n-phenyldithiocarbamate of Cu(II), the methyl-n-hexyldithiocarbamate of Cu(II), the methylphenyldithiocarbamate of Cu(II) the ethyl-n-propyldithiocarbamate of Cu(II), the ethyl-n-butyl-dithiocarbamate of Cu(II), the ethyl-n-pentyldithiocarbamate of Cu(II), the ethyl-n-hexyldithiocarbamate of Cu(II), the ethylphenyldithiocarbamate of Cu(II), the n-propyl-n-butyldithiocarbamate of Cu(II), the n-propyl-n-pentyldithiocarbamate of Cu(II), the n-propyl-n-hexyldithiocarbamate of Cu(II), the n-propylphenyldithiocarbamate of Cu(II), the n-butyl-n-pentyldithiocarbamate of Cu(II), the n-butyl-n-hexyl-dithiocarbamate of Cu(II), the n-butylphenyldithiocarbamate of Cu(II), the n-pentyl-n-hexyldithiocarbamate of Cu(II), the n-pentylphenyldithiocarbamate of Cu(II) and the n-hexylphenyldithiocarbamate of Cu(II), and also the bis(2-hydroxyethyl)dithiocarbamate of Cu(II).

85. The process according to any of embodiments 1 to 82, wherein the at least one chemical compound of the element copper is a salt.
86. A liquid phase P which comprises at least one chemical compound of the element copper and is obtainable by a process according to any of embodiments 1 to 85.
87. A liquid phase P whose acrylic acid content is at least 10% by weight and which, based on the weight of the acrylic acid present therein, additionally comprises at least 100 ppm by weight of propionic acid, at least 100 ppm by weight of glyoxal, optionally at least 100 ppm by weight of diacrylic acid, and at least one chemical compound of the element copper.
88. The liquid phase P according to embodiment 86 or 87, which additionally comprises one or more inhibitors from the group consisting of nitroxyl radicals, the phenothiazines, the phenolic compounds, molecular oxygen, the cerium(III) salts, the manganese(III) salts, the p-phenylenediamines, methylene blue and the organic nitroso compounds.
89. The liquid phase P according to any of embodiments 86 to 88, which comprises, based on the weight of the weight of acrylic acid present therein, additionally 50 to 1000 ppm by weight of phenothiazine.

U.S. Provisional Application No. 61/391,102, filed Oct. 8, 2010, is incorporated into the present specification by literature reference. In light of the above teachings, many amendments and variations of the present invention are possible. It may therefore be assumed that the invention can, within the appended claims, be operated otherwise than as specifically described herein.

EXAMPLES AND COMPARATIVE EXAMPLES

1. Preparation of Liquid Phases P with Different Added Polymerization Inhibitors, and of Differently Inhibited Liquid Comparative Phases Glacial acrylic acid freshly prepared as described in DE-A 102007055086, which, based on its weight, had been polymerization-inhibited with 200 ppm by weight of methoxyphenol (MEHQ), was freed of MEHQ under reduced pressure (1000 Pa) by distilling it over twice in succession.

The purity of the glacial acrylic acid distillate GD thus obtained was >99.8% by weight, with a total aldehyde and ketone content of <5 ppm by weight, a diacrylic acid content of <1 ppm by weight and a propionic acid content of 190 ppm by weight.

A portion of the glacial acrylic acid distillate GD was divided into identical samples of 1 ml.

Another portion was used to produce different stock solutions in which, for example, different amounts of different polymerization inhibitors had been dissolved. A further portion of the glacial acrylic acid distillate was used to produce a stock solution with added propionic acid (purity >99.5% by weight).

In a corresponding manner, a glyoxal-comprising stock solution was produced. The glyoxal source used for that purpose was an aqueous solution from Aldrich, which, according to the manufacturer's information, comprised 40% by weight of dissolved glyoxal (calculated as monomeric glyoxal). The preparation of this stock solution was accompanied by slight precipitate formation, which was probably caused by high molecular weight polyglyoxals (or hydrates thereof) which are sparingly soluble in the glacial acrylic acid GD. Therefore, the precipitate formed was filtered off and then the glyoxal content of the filtrate was determined as described in this document (1 g of the 40% by weight aqueous glyoxal solution were added at 25° C. to 60 g of glacial acrylic acid distillate GD; then the mixture was stirred at 25° C. for 15 min; then the precipitate formed was filtered off).

Samples taken from the stock solutions were diluted with the glacial acrylic acid distillate GD in the amount required in each case, and the dilutions were used to dope the different 1 ml samples as desired. Subsequently, the doped samples were preserved by freezing. Some samples were left to stand at 35° C. in order to increase their content of diacrylic acid.

2. Study of the Polymerization Tendency of the Samples of the Different Liquid Phases To study the polymerization tendency of the particular doped sample, it was liquefied again and an HPLC vial (transparent vessel of capacity 1.5 ml) was charged in each case with 0.5 ml of the particular sample under air and then sealed tight with a crimp cap. Immediately after completion, in each case up to six vials charged as described were suspended in a holder produced therefor and left to stand at a temperature of 120° C. in a forced-air drying cabinet, while the holder rotated at six revolutions per minute in order to ensure complete mixing in the vials (the liquid contents of the particular vial came into contact with the crimp cap six times per minute). Then the time T until complete polymerization of the particular sample in the corresponding vial was detected. For this purpose, the samples in the vials in the drying cabinet were monitored with the aid of a video camera (the maximum film duration was 720 minutes), and the video film was subsequently evaluated visually.

Each test was repeated three times and the corresponding values for T were averaged arithmetically. The resulting mean values T (in minutes) for the different samples, including their corresponding relevant contents of constituents other than acrylic acid, are listed below (the amounts stated are based in each case on the amount of acrylic acid present in the particular sample).

The following abbreviations were used:

PA = propionic acid
DA = diacrylic acid
Gly = glyoxal
PTZ = phenothiazine
Cu(Ac)$_2$ = Cu(II) acetate
CuAc = Cu(I) acetate
Ce(Ac)$_3$ = cerium(III) acetate
Fe(Ac)$_2$ = Fe(II) acetate Mn (Ac)$_3$ = Mn(III) acetate
NiSO$_4$ = Ni(II) sulfate
Nadetc = sodium diethyldithiocarbamate
CuGluc = Cu(II) gluconate
CuTart = Cu(II) tartrate monohydrate
CuAcetyl = Cu(II) acetylacetonate
Cudetc = Cu(II) diethyldithiocarbamate
Cudbtc = Cu(II) di-n-butyldithiocarbamate
Cub(2he)dtc = Cu(II) bis(2-hydroxyethyl)di-thiocarbamate

| Sample | T (min) |
|---|---|
| GD with 190 ppm by weight of PA | 20 |
| GD with 190 ppm by weight of PA, 50 ppm by weight of Gly | 16 |
| GD with 190 ppm by weight of PA, 10 ppm by weight of PTZ | 162 |
| GD with 190 ppm by weight of PA, 5 ppm by weight of Gly, 10 ppm by weight of PTZ | 130 |
| GD with 190 ppm by weight of PA, 80 ppm by weight of Gly, 10 ppm by weight of PTZ | 99 |
| GD with 190 ppm by weight of PA, 1.52 molar ppm of Cu (as Cudbtc) | 70 |
| GD with 190 ppm by weight of PA, 5 ppm by weight of Gly, 1.52 molar ppm of Cu (as Cudbtc) | 80 |
| GD with 190 ppm by weight of PA, 80 ppm by weight of Gly, 1.52 molar ppm of Cu (as Cudbtc) | 105 |
| GD with 190 ppm by weight of PA, 200 ppm by weight of Gly, 1.52 molar ppm of Cu (as Cudbtc) | 142 |
| GD with 190 ppm by weight of PA, 500 ppm by weight of Gly, 1.52 molar ppm of Cu (as Cudbtc) | >720 |
| GD with 300 ppm by weight of PA, 64 ppm by weight of DA, 500 ppm by weight of Gly, 1.52 molar ppm of Cu (as Cudbtc) | >720 |
| GD with 190 ppm by weight of PA, 3.97 molar ppm of Cu (as Cu(Ac)$_2$) | 113 |
| GD with 190 ppm by weight of PA, 250 ppm by weight of Gly, 10 ppm by weight of PTZ, 3.97 molar ppm of Cu (as Cu(Ac)$_2$) | 270 |
| GD with 190 ppm by weight of PA, 500 ppm by weight of Gly, 10 ppm by weight of PTZ, 3.97 molar ppm of Cu (as Cu(Ac)$_2$) | 353 |
| GD with 190 ppm by weight of PA, 10 ppm by weight of PTZ, 3.97 molar ppm of Cu (as Cu(Ac)$_2$) | 161 |
| GD with 190 ppm by weight of PA, 100 ppm by weight of Gly, 10 ppm by weight of PTZ | 84 |
| GD with 190 ppm by weight of PA, 100 ppm by weight of Gly, 10 ppm by weight of PTZ, 0.76 molar ppm of Cu (as Cudbtc) | 125 |
| GD with 190 ppm by weight of PA, 100 ppm by weight of Gly, 10 ppm by weight of PTZ, 1.52 molar ppm of Cu (as Cudbtc) | 139 |
| GD with 190 ppm by weight of PA, 100 ppm by weight of Gly, 10 ppm by weight of PTZ, 3.80 molar ppm of Cu (as Cudbtc) | 157 |
| GD with 190 ppm by weight of PA, 100 ppm by weight of Gly, 10 ppm by weight of PTZ, 7.60 molar ppm of Cu (as Cudbtc) | 180 |
| GD with 190 ppm by weight of PA, 100 ppm by weight of Gly, 10 ppm by weight of PTZ, 15.2 molar ppm of Cu (as Cudbtc) | 196 |
| GD with 190 ppm by weight of PA, 100 ppm by weight of Gly, 10 ppm by weight of PTZ, 76 molar ppm of Cu (as Cudbtc) | 228 |
| GD with 190 ppm by weight of PA, 100 ppm by weight of Gly, 10 ppm by weight of PTZ, 152 molar ppm of Cu (as Cudbtc) | 311 |
| GD with 190 ppm by weight of PA, 500 ppm by weight of Gly, 10 ppm by weight of PTZ | 61 |
| GD with 190 ppm by weight of PA, 500 ppm by weight of Gly, 10 ppm by weight of PTZ, 3.42 molar ppm of Cu (as Cudbtc) | 440 |
| GD with 190 ppm by weight of PA, 500 ppm by weight of Gly, 10 ppm by weight of PTZ, 18.9 ppm by weight of Nadetc | 50 |
| GD with 190 ppm by weight of PA, 1000 ppm by weight of Gly, 10 ppm by weight of PTZ, 1.90 molar ppm of Cu (as Cu(I)Ac) | 335 |
| GD with 190 ppm by weight of PA, 1000 ppm by weight of Gly, 10 ppm by weight of PTZ, 1.90 molar ppm of Cu (as CuGluc) | 204 |
| GD with 190 ppm by weight of PA, 1000 ppm by weight of Gly, 10 ppm by weight of PTZ, 1.70 molar ppm of Cu (as CuAcetyl) | 246 |
| GD with 190 ppm by weight of PA, 1000 ppm by weight of Gly, 10 ppm by weight of PTZ, 1.50 molar ppm of Cu (as CuTart) | 179 |
| GD with 190 ppm by weight of PA, 500 ppm by weight of Gly, 10 ppm by weight of PTZ, 3.70 molar ppm of Cu (as Cub(2he)dtc) | 439 |
| GD with 190 ppm by weight of PA, 10 ppm by weight of PTZ, 10 ppm by weight of NiSO$_4$ | 142 |
| GD with 190 ppm by weight of PA, 500 ppm by weight of Gly, 10 ppm by weight of PTZ, 10 ppm by weight of NiSO$_4$ | 38 |
| GD with 190 ppm by weight of PA, 500 ppm by weight of Gly, 10 ppm by weight of NiSO$_4$ | 15 |
| GD with 190 ppm by weight of PA, 10 ppm by weight of Gly, 10 ppm by weight of PTZ, 10 ppm by weight of Ce(Ac)$_3$ | >720 |
| GD with 190 ppm by weight of PA, 500 ppm by weight of Gly, 10 ppm by weight of PTZ, 10 ppm by weight of Ce(Ac)$_3$ | 161 |
| GD with 190 ppm by weight of PA, 500 ppm by weight of Gly, 10 ppm by weight of Ce(Ac)$_3$ | 33 |
| GD with 190 ppm by weight of PA, 10 ppm by weight of PTZ, 10 ppm by weight of Fe(Ac)$_2$ | 125 |
| GD with 190 ppm by weight of PA, 500 ppm by weight of Gly, 10 ppm by weight of PTZ, 10 ppm by weight of Fe(Ac)$_2$ | 36 |
| GD with 190 ppm by weight of PA, 500 ppm by weight of Gly, 10 ppm by weight of Fe(Ac)$_2$ | 10 |
| GD with 190 ppm by weight of PA, 10 ppm by weight of PTZ, 10 ppm by weight of Mn(Ac)$_3$ | >720 |
| GD with 190 ppm by weight of PA, 500 ppm by weight of Gly, 10 ppm by weight of PTZ, 1 ppm by weight of Mn(Ac)$_3$ | 265 |
| GD with 190 ppm by weight of PA, 500 ppm by weight of Gly, 10 ppm by weight of Mn(Ac)$_3$ | 12 |
| GD with 625 ppm by weight of PA, 119 ppm by weight of DA, 500 ppm by weight of Gly, 10 ppm by weight of PTZ, 3.97 molar ppm of Cu (as Cu(Ac)$_2$) | 490 |

A corresponding retarding action to that of glyoxal in the presence of copper-comprising compounds was also detected in corresponding doping tests for hydroxyacetone, glycolaldehyde, glycerolaldehyde, 1,3-dihydroxyacetone and glutaraldehyde. 3-hydroxybenzaldehyde already has retarding action on acrylic acid. Salicylaldehyde and o-phthalaldehyde, which, just like 3-hydroxybenzaldehyde, may be the by-product of a heterogeneously catalyzed partial oxidation of $C_3$ precursor compounds to acrylic acid, in contrast, promote the unwanted free-radical polymerization of acrylic acid.

The invention claimed is:
1. A process, comprising:
adding at least one chemical compound that comprises copper to a liquid phase P, said liquid phase P comprises acrylic acid, propionic acid, and glyoxal, thereby inhibiting free-radical polymerization of acrylic acid in liquid phase P, wherein
said acrylic acid is present in said liquid phase P in an amount of at least 10% by weight of said liquid phase P,
said propionic acid is present in said liquid phase P in an amount of at least 100 ppm by weight,
said glyoxal is present in said liquid phase P in an amount of at least 100 ppm by weight, and
each copper atom of the at least one chemical compound has an oxidation state of +1 or +2.

2. The process according to claim 1, wherein the at least one chemical compound is present in said liquid phase P in an amount, based on the molar amount of acrylic acid present therein, of from 0.01 molar ppm to 5 mol % of Cu.

3. The process according to claim 1, wherein the at least one chemical compound is present in said liquid phase P in dispersed form, in dissolved form, or in a combination thereof.

4. The process according to claim 1, wherein the liquid phase P further comprises at least 1% by weight of water.

5. The process according to claim 1, wherein the liquid phase P, based on the weight of the acrylic acid present therein, further comprises ≥100 ppm by weight of diacrylic acid.

6. The process according to claim 1, wherein the acrylic acid present in the liquid phase P is the product of a heterogeneously catalyzed partial oxidation of a $C_3$ precursor compound of acrylic acid, in which a starting reaction gas mixture which is used for the partial oxidation and comprises the $C_3$ precursor compound, based on the molar amount of the $C_3$ precursor compound present therein, has a total molar amount of $C_2$ compounds of ≥100 molar ppm.

7. The process according to claim 6, wherein the $C_3$ precursor compound is propylene, acrolein or n-propane.

8. The process according to claim 1, wherein the acrylic acid present in the liquid phase P is the product of a heterogeneously catalyzed partial oxidation of a $C_3$ precursor compound of acrylic acid, in which a starting reaction gas mixture which is used for the partial oxidation and comprises the $C_3$ precursor compound, based on the molar amount of the $C_3$ precursor compound present therein, has a total molar amount of cyclopropane of ≥10 molar ppb.

9. The process according to claim 1, wherein the acrylic acid present in the liquid phase P is the product of a heterogeneously catalyzed partial oxidation of a $C_3$ precursor compound of acrylic acid, in which a starting reaction gas mixture which is used for the partial oxidation and comprises the $C_3$ precursor compound comprises up to 80% by volume of n-propane.

10. The process according to claim 1, wherein the at least one chemical compound is in the form of a salt.

11. The process according to claim 1, wherein the at least one chemical compound is present in said liquid phase P in an amount, based on the molar amount of acrylic acid present therein, of from 0.1 molar ppm to 100 molar ppm of Cu.

12. The process according to claim 1, wherein said acrylic acid is present in said liquid phase P in an amount of at least 90% by weight of said liquid phase P.

13. The process according to claim 1, wherein said acrylic acid is present in said liquid phase P in an amount of at least 98% by weight of said liquid phase P.

14. The process according to claim 1, wherein said glyoxal is present in said liquid phase P in an amount of from 100 to 2,500 ppm by weight.

15. The process according to claim 1, wherein the liquid phase P further comprises from 1% to 5% by weight of water.

16. The process according to claim 1, wherein said propionic acid is present in said liquid phase P in an amount of from 150 to 2500 ppm.

17. The process according to claim 1, wherein the at least one chemical compound is present in said liquid phase P in an amount, based on the molar amount of acrylic acid present therein, of from 0.1 molar ppm to 10 molar ppm of Cu.

18. A liquid phase P whose acrylic acid content is at least 10% by weight and which, based on the weight of the acrylic acid present therein, additionally comprises at least 100 ppm by weight of propionic acid, at least 100 ppm by weight of glyoxal, optionally at least 100 ppm by weight of diacrylic acid, and at least one chemical compound of the element copper.

19. The liquid phase P according to claim 18, which additionally comprises at least one inhibitor selected from the group consisting of a nitroxyl radical, a phenothiazine, a phenolic compound, molecular oxygen, as cerium(III) salt, a manganese(III) salt, a phenylenediamine, methylene blue, and an organic nitroso compound.

20. The liquid phase P according to claim 18, which comprises, based on the weight of the acrylic acid present therein, additionally 50 to 1000 ppm by weight of phenothiazine.

21. The liquid phase P according to claim 18, wherein the at least one chemical compound of the element copper is present in said liquid phase P in an amount, based on the molar amount of acrylic acid present therein, of from 0.01 molar ppm to 5 mol % of Cu.

22. The liquid phase P according to claim 18, wherein the at least one chemical compound of the element copper is present in said liquid phase P in dispersed form, in dissolved form, or in a combination thereof.

23. The liquid phase P according to claim 18, which further comprises at least 1% by weight of water.

24. The liquid phase P according to claim 18, which further comprises, based on the weight of the acrylic acid present therein, ≥100 ppm by weight of diacrylic acid.

25. The liquid phase P according to claim 18, wherein the acrylic acid present in the liquid phase P is the product of a heterogeneously catalyzed partial oxidation of a $C_3$ precursor compound of acrylic acid, in which a starting reaction gas mixture which is used for the partial oxidation and comprises the $C_3$ precursor compound, based on the molar amount of the $C_3$ precursor compound present therein, has a total molar amount of $C_2$ compounds of ≥100 molar ppm.

26. The liquid phase P according to claim 25, wherein the $C_3$ precursor compound is propylene, acrolein or n-propane.

27. The liquid phase P according to claim 18, wherein the acrylic acid present in the liquid phase P is the product of a heterogeneously catalyzed partial oxidation of $C_3$ precursor compound of acrylic acid, in which a starting reaction gas mixture which is used for the partial oxidation and comprises the $C_3$ precursor compound, based on the molar amount of the $C_3$ precursor compound present therein, has a total molar amount of cyclopropane of ≥10 molar ppb.

28. The liquid phase P according to claim 18, wherein the acrylic acid present in the liquid phase P is the product of a heterogeneously catalyzed partial oxidation of $C_3$ precursor compound of acrylic acid, in which a starting reaction gas mixture which is used for the partial oxidation and comprises the $C_3$ precursor compound comprises up to 80% by volume of n-propane.

29. The liquid phase P according to claim 18, wherein the at least one chemical compound is in the form of a salt.

30. The liquid phase P according to claim 18, wherein the at least one chemical compound is present in said liquid phase P in an amount, based on the molar amount of acrylic acid present therein, of from 0.1 molar ppm to 100 molar ppm of Cu.

31. The liquid phase P according to claim 18, wherein said acrylic acid is present in said liquid phase P in an amount of at least 90% by weight of said liquid phase P.

32. The liquid phase P according to claim 18, wherein said acrylic acid is present in said liquid phase P in an amount of at least 98% by weight of said liquid phase P.

33. The liquid phase P according to claim 18, wherein said glyoxal is present in said liquid phase P in an amount of from 100 to 2,500 ppm by weight.

34. The liquid phase P according to claim 18, wherein the liquid phase P further comprises from 1% to 5% by weight of water.

35. The liquid phase P according to claim 18, wherein said propionic acid is present in said liquid phase P in an amount of from 150 to 2500 ppm.

36. The liquid phase P according to claim 18, wherein the at least one chemical compound is present in said liquid phase P in an amount, based on the molar amount of acrylic acid present therein, of from 0.1 molar ppm to 10 molar ppm of Cu.

* * * * *